(12) United States Patent
Campagna et al.

(10) Patent No.: US 9,436,991 B2
(45) Date of Patent: Sep. 6, 2016

(54) METHOD, DEVICE AND SYSTEM FOR OBTAINING A MEDICAL IMAGE DATA SET

(71) Applicant: Siemens Aktiengesellschaft, Munich (DE)

(72) Inventors: Swen Campagna, Engelthal (DE); Peter Stransky, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/480,916

(22) Filed: Sep. 9, 2014

(65) Prior Publication Data

US 2015/0071518 A1 Mar. 12, 2015

(30) Foreign Application Priority Data

Sep. 9, 2013 (DE) .................... 10 2013 217 935

(51) Int. Cl.
*G06K 9/00* (2006.01)
*G06T 7/00* (2006.01)
*H04N 19/42* (2014.01)
*G06F 19/00* (2011.01)

(52) U.S. Cl.
CPC .......... *G06T 7/0012* (2013.01); *G06F 19/321* (2013.01); *H04N 19/42* (2014.11); *G06T 2210/41* (2013.01); *G06T 2211/40* (2013.01)

(58) Field of Classification Search
None
See application file for complete search history.

(56) References Cited

U.S. PATENT DOCUMENTS

| 2003/0228041 A1* | 12/2003 | Bae ................... G06T 9/007 |
| | | 382/131 |
| 2005/0111746 A1 | 5/2005 | Kumar et al. |
| 2011/0081065 A1 | 4/2011 | Canstein |

OTHER PUBLICATIONS

Kau et al..; "A Cloud Computing-Based Image Codec System for Lossless Compression of Images on a Cortex-A8 Platform"; BiOCAS; pp. 288-291; (2012).
Heo,et al. "Improved Cabac Design in H.264/AVC for Lossless Depth Map Coding"; IEEE International Conference on Multimedia and Expo (ICME); pp. 1-4; 2011.
"Network Abstraction Layer"; Wikipedia; (2013).

* cited by examiner

*Primary Examiner* — Stephen R Koziol
*Assistant Examiner* — Amandeep Saini
(74) *Attorney, Agent, or Firm* — Schiff Hardin LLP

(57) ABSTRACT

In a method, device and system for obtaining a medical image data set, a raw data stream is produced by a data acquisition device, the raw data stream including at least digital data of a medical raw data image set. The raw data stream is provided to a data compression device, wherein it is compressed. The compressed raw data stream is transferred to a data decompression device, wherein it is decompressed. The decompressed raw data stream is transferred to an image calculation tool, which produces a medical image data set operating on the decompressed raw data stream.

10 Claims, 3 Drawing Sheets

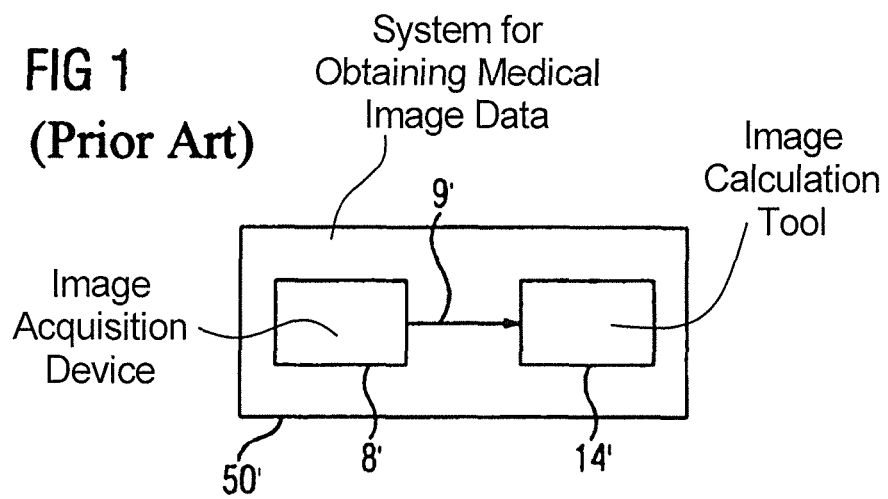
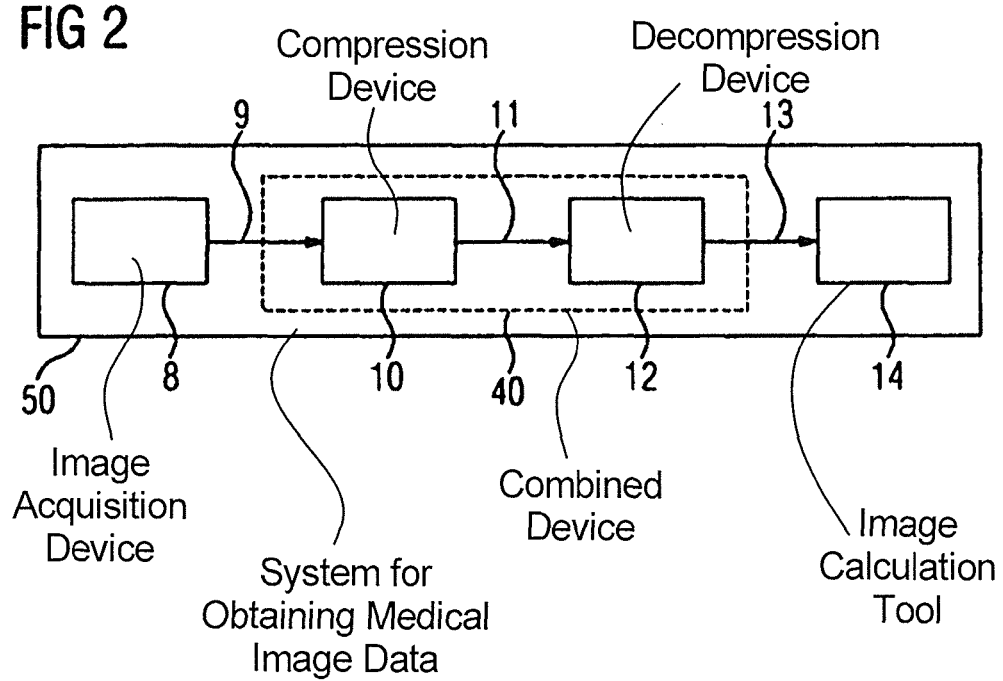

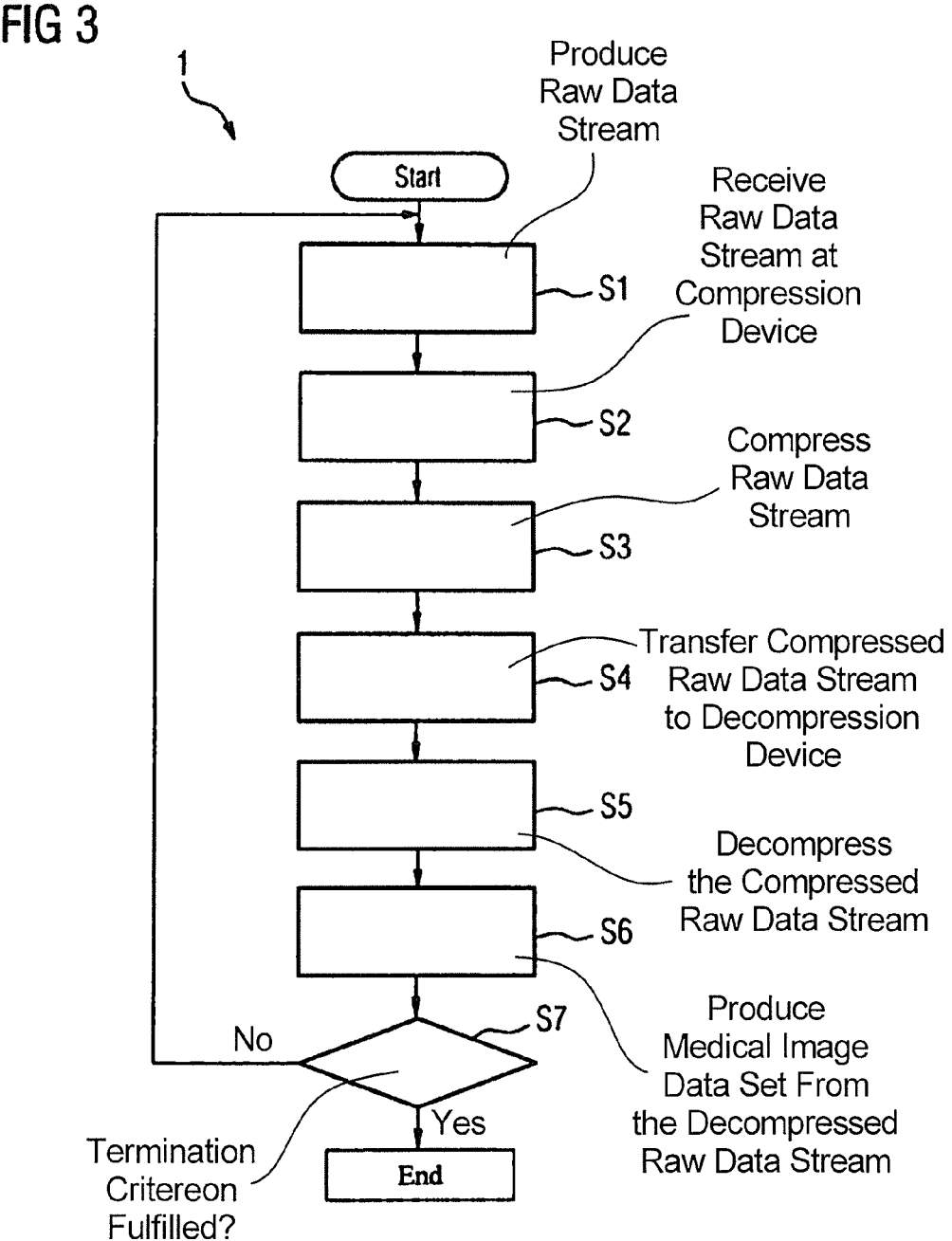

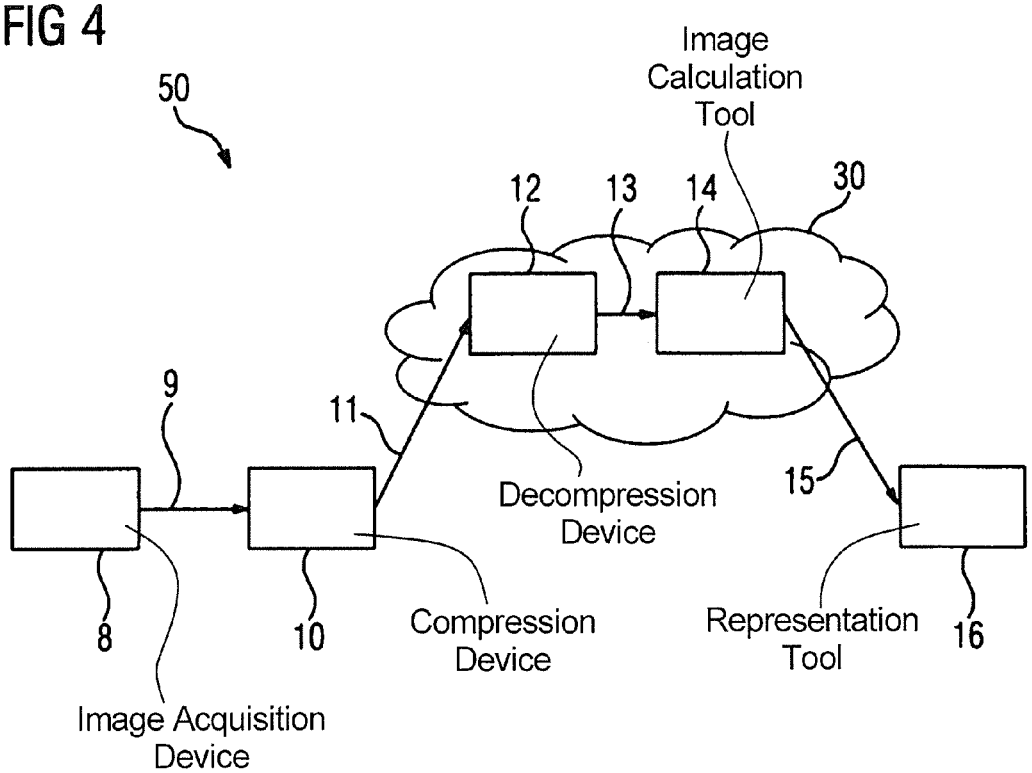
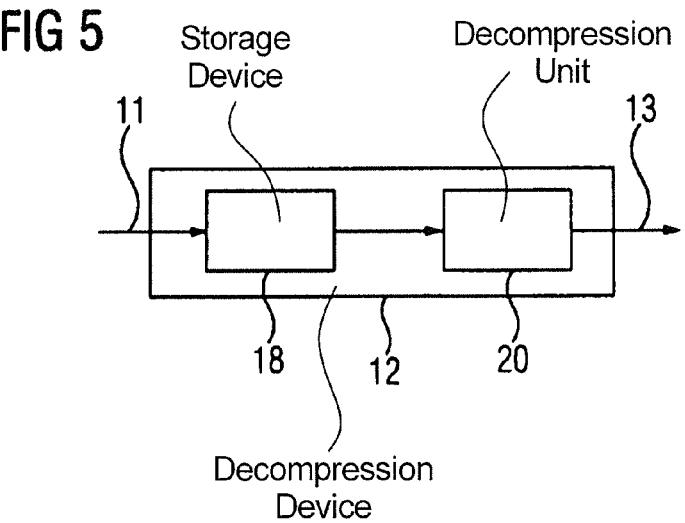

METHOD, DEVICE AND SYSTEM FOR OBTAINING A MEDICAL IMAGE DATA SET

BACKGROUND OF THE INVENTION

1. Field of the Invention

The present invention relates to a method for obtaining a medical image data set. In addition, the present invention relates to a device and a system for obtaining a medical image data set.

2. Description of the Prior Art

When acquiring medical images, for example, with a modern x-ray apparatus, a computed tomography, (CT) scanner, and magnetic resonance imaging (MRI) device, a large amount of data is generated. Here a distinction is made between a raw data acquisition and further image processing, for example, image reconstruction. When obtaining a medical image, for example, by means of an MR measurement, raw data are obtained, which come directly from an image converter, in the case of an MR device MR signals detected (acquired) by receiving antennas, or which come from downstream, relatively simple image processing devices, for example, an analog-to-digital converter, so the data are available in digital form. The raw data of the imaging device can be supplemented by further administrative and/or metadata, for example, a time stamp, channel information, etc. In an MR system with, for example, 128 receiving channels, it is currently possible to obtain up to 512 MB/sec of raw data, depending on measurement and parameterization. Generally, the raw data are not comprehensible for a human viewer, for example, a physician. They have to be first transferred, for example, to a spatial image data set through very complex further processing. Depending on the complexity of this further processing, for example, MR image reconstruction, high technical requirements are placed on the devices performing the process of further processing, and/or the entire or part of the data volume has to be stored temporarily on appropriate storage systems for further processing, or the data volume has to transferred to different computers.

Usually, the data volume has to be stored and/or transferred in its entirety. The storage media or network connections have to be dimensioned in accordance with the data volume and/or data rates to be expected. As a data buffer, it is common to use, for example, a so-called hard drive RAID system, which is configured from a specific number of hard drives on which the data volume is stored with the use of parallel write access.

SUMMARY OF THE INVENTION

An object of the present invention is to provide a method that, compared to previous methods, allows for the use of technical devices with lower requirements when obtaining a medical image data set. Furthermore, an object of the present invention is to provide an appropriate device and an appropriate system for implementing such a method.

The basis of the invention is a method for obtaining a medical image data set, which makes use of an image acquisition device, a data compression device, a data decompression device and an image calculation tool. The method involves the following processing steps:

S1) producing a raw data stream with of the data acquisition device, wherein the raw data stream comprises at least digital data of a medical raw data image set;

S2) receiving the raw data stream of the image acquisition device with the data compression device;

S3) compressing the raw data stream in the data compression device;

S4) transferring the compressed raw data stream to the data decompression device;

S5) decompressing the compressed raw data stream in the data decompression device;

S6) transferring the decompressed raw data stream to the image calculation tool and producing a medical image data set by operating of the image calculation tool on the decompressed raw data stream.

Therefore, according to the method, there is at least an image acquisition device, a data compression device, a data decompression device and an image calculation tool. Generally, the image acquisition device involves a well-known image data detector or any device that can be used to acquire medical image information, wherein the image information, which can also be interpreted as raw image data, can be transformed into digital data by the image acquisition device. In the first processing step, a raw data stream that includes at least the digital data of the medical raw data image set is produced by the image acquisition device. In the second processing step, the data compression device receives the raw data stream of the image acquisition device. For example, this can be achieved by using a data bus between the image acquisition device and the data compression device, as well as a well-known data transfer protocol. In the third processing step, the raw data stream is compressed by the data compression device. Compression methods are well-known methods used to compress a data stream or data volume, i.e., to reduce the amount of data or the amount of data to be transferred, without significantly changing the content of the information. In the fourth processing step, the data compression device transfers the compressed or reduced raw data stream to the data decompression device. Because of the fact that the compressed raw data stream is usually smaller than the non-compressed raw data stream, a lower data rate is required to transfer the same information. In the fifth processing step, the compressed raw data stream is decompressed by means of the data decompression device, i.e., the original information content is restored. The decompression algorithm used is matched to the compression algorithm that is used. In the sixth processing step, the decompressed raw data stream is transferred to the image calculation tool, which produces a medical image data set in a generally known manner.

It is preferred to perform the processing steps S1 to S6 repeatedly until a termination criterion tested in accordance with processing step S6, has been fulfilled.

The method can be performed repeatedly, or individual processing steps can be performed in parallel fashion. For example, it is possible to continuously supply data from the image acquisition device to the data compression device, the data compression device can continuously compress the data received and transfer the compressed data to the data decompression device. A termination criterion can involve checking for the end of the raw data stream. When the image acquisition device stops supplying raw data, the end of the raw data stream has been reached, the termination criterion is fulfilled and the method is terminated. Further termination criteria can involve, for example, that an operator actuates a push-button or that a predetermined meter reading is achieved, wherein the meter, for example, represents the data volume to be transferred.

In a further embodiment, the raw data stream is compressed by the data compression device, using a loss-free compression method.

In principal, it is possible to use two different types of compression methods, namely compression methods with or without losses.

The advantage of loss-free compression methods, or compression methods without losses, is that numerous, generally known methods are already available. As indicated by the name, after the compression it is possible to achieve, by a decompression, an exact bit-by-bit reconstruction of the content. For example, by the loss-free compression, it is possible to reduce the data volume of MR raw data by between 25% and 50%.

By using lossy compression, it is generally possible to further reduce the data volume, i.e., the compression rate is even higher than with loss-free compression. However, the information of a lossy compressed data set, which is subsequently decompressed, generally cannot be reconstructed bit-by-bit, resulting in errors in further processing.

In a further advantageous embodiment, the raw data stream includes digital data of a medical image data set and additional data. The additional data include information about the image acquisition device and/or additional data regarding the production of the raw data stream.

In this embodiment, further information is transferred in addition to the actual image data, for example, the time of image generation, i.e., a time stamp, or channel information, or a parameter of the imaging device or the acquisition, for example, exposure times, or an internal parameter of the device. If additional data are transferred, the data stream is preferably compressed with a loss-free compression method because bit errors can render such metadata unusable. When using a loss-free compression method, the semantics of the data stream are unimportant.

In an alternative embodiment of the invention, the digital data of a medical image data set are compressed by a lossy compression method, and the additional data are compressed by means of a loss-free compression method.

With this embodiment, it is possible to use the advantages of both compression methods. For image data it can be acceptable to distort data with a lossy compression and decompression process, because the imaging method involves already inherently takes into account that a certain degree of noise is superimposed on the image data. In a lossy compression process, the data are generally more compressed than in a loss-free compression process. For the compression of additional data or metadata, a loss-free compression is used, resulting in an error-free reconstruction of the data.

The data compression device can include storage devices, and at least part of the compressed raw data stream is stored temporarily prior to processing step S5.

Generally, the compressed raw data stream is considerably smaller than the original raw data stream so that, prior to the decompression process by the decompression device, this smaller data volume requires less storage space than storing the original raw data stream. Storing the compressed raw data stream results in the subsequent processing media, for example, the image calculation tool not requiring the high performance, which would be needed for processing the original raw data stream.

In a further advantageous embodiment, that the data compression device and the image calculation tool are part of a Cloud Computing Network, and after the processing step S6, the medical image data set produced is transferred to a calculation and representation tool.

Cloud Computing Networks are generally well-known structures in which abstracted IT infrastructures, such as computing capacity, data storage, network capacities, are made available via a network and dynamically adapted to the respective requirement. In the context of the invention, the data compression device and the image calculation tool can be in the so-called Cloud, so as to perform the respective processing step in the Cloud and to obtain the results from the Cloud. Advantageously, instead of the original raw data stream, only the compressed raw data stream has to be transferred to the Cloud.

In an alternative embodiment of the invention, by executing a software program, the raw data stream is compressed the data compression device and/or the compressed raw data stream is decompressed the data decompression device.

In principle, it is possible to perform the compression of the original raw data stream and/or the decompression of the compressed raw data stream with special electronic circuits, for example, FPGA circuits, or the respective methods are represented by computer programs and are performed by computers or microcontrollers. Advantageously, the compression of the original raw data stream is performed by a computer program, which can be executed in the image acquisition device, and/or the decompression of the compressed raw data stream is performed by a computer program, which can be executed in the image calculation device. It is also possible to use one or multiple calculation devices, for example, computers, in order to perform the respective calculations.

The invention also concerns a device for obtaining a medical image data set. The device has a data compression device and a data decompression device. The data compression device is designed to receive a raw data stream of an image acquisition device, wherein the raw data stream comprises at least digital data of a medical raw image data set, to compress the raw data stream to a compressed raw data stream, and to transfer the compressed raw data stream to the data decompression device. The data decompression device is designed to decompress the raw data stream, and to transfer the decompressed raw data stream to an image calculation tool for producing a medical image data set.

The device for obtaining a medical image data set is integrated in an image acquisition device, which supplies a raw data stream, and an image calculation tool, which receives the decompressed compressed raw data stream. The device compresses the original raw data stream, transfers the reduced raw data stream, which requires a small band width, and reconstructs the compressed raw data stream after the transfer, implying to the image calculation tool that it is obtaining the original raw data stream.

The device is designed to perform one or more of the embodiments of the method described above.

For example, the device can include storage devices, such as hard drive memories or semiconductor memories, which store temporarily the compressed raw data stream, so that subsequent calculation devices do not have to process the data in real time, thus requiring less computing power.

The invention also concerns a system for obtaining a medical image data set. The system includes an image acquisition device, a data compression device, a data decompression device and an image calculation tool. The image acquisition device is designed to produce a raw data stream, wherein the raw data stream comprises at least digital data of a medical raw image data set, and to make the raw data stream available to a data compression device. The data compression device is designed to receive the raw data stream of the image acquisition device, to compress the raw data stream to a compressed raw data stream, and to transfer the compressed raw data stream to the data decompression device. The data decompression device is designed to decompress the compressed raw data stream, and to make the decompressed raw data stream available to the image calculation tool. The image calculation tool is designed to receive the decompressed raw data stream and produce therefrom a medical image data set.

Consequently, the system for obtaining a medical image data set has an image acquisition device, a data compression device, a data decompression device and an image calculation tool. Because of the fact that the original raw data stream has been compressed, only a small data volume has to be transferred to subsequent devices, making it sufficient to use technical devices with these lower requirements.

The system is designed to perform one or more of the embodiments of the method described above.

For example, parts of the system for obtaining a medical image data set can be implemented in the so-called Computer Cloud. By compressing the original raw data stream, only a smaller data volume has to be transferred to the Cloud, where the data is decompressed and processed further.

In an advantageous embodiment, the image acquisition device is a magnetic resonance imaging apparatus.

When obtaining a medical image by operation of magnetic resonance imaging apparatus, raw data are generated with a high data rate, which have to be stored temporarily in storage devices with high storage capacity and/or processed in real time with high capacity computers. The invention described above is especially useful in this field.

BRIEF DESCRIPTION OF THE DRAWINGS

FIG. 1 schematically illustrates a system for obtaining a medical image data set in accordance with prior art.

FIG. 2 schematically illustrates an embodiment of an inventive system for obtaining a medical image data set.

FIG. 3 is an example of a flowchart of an inventive method for obtaining a medical image data set.

FIG. 4 schematically illustrates an embodiment of an inventive system for obtaining a medical image data set connected to a Cloud Computing Network.

FIG. 5 schematically illustrates an embodiment of a data compression device, which has a storage device.

DETAILED DESCRIPTION OF THE INVENTION

FIG. 1 shows a schematic illustration of a system 50' for obtaining a medical image data set in accordance with prior art. An image acquisition device 8', for example, magnetic resonance imaging equipment, produces a raw data stream 9', which is transferred to an image calculation tool 14', for example, a computer. For example, from the transferred raw data, the image calculation tool 14' calculates with well-known algorithms a spatial medical image. At the same time, the image calculation tool 14' has to process the transferred raw data as fast as they are provided by the image acquisition device 8' or a sufficiently large storage capacity has to be provided to store the data temporarily for slower subsequent processing.

FIG. 2 is a schematic illustration of an inventive system 50 for obtaining a medical image data set. The system 50 has an image acquisition device 8, for example, magnetic resonance imaging equipment, a data compression device 10, for example, an electronic circuit, a data decompression device 12, for example, a computer, on which a method for data compression is processed, and an image calculation tool 14, for example, also a computer, on which image reconstruction methods are processed. It is also possible that the data decompression device 12 and the image calculation tool 14 to be physically attached to a computer and the various methods are processed on different computer cores. The image acquisition device 8 produces a raw data stream 9, that includes at least the digital data of a medical raw image data set, and makes the raw data stream 9 available to the data compression device 10. The data compression device 10 receives the raw data stream 9 of the image acquisition device 8. For example, this can be achieved by using a data bus between the image acquisition device 8 and the data compression device 10, as well as a well-known data transfer protocol. Using a loss-free compression algorithm, the data compression device 10 compresses the raw data stream to a compressed raw data stream 11. Compression methods are well-known methods used to compress a data stream or a data volume, i.e., to reduce the amount of data or the amount of data to be transferred. The compressed or reduced raw data stream 11 is transferred from the data compression device 10 to the data decompression device 12. Because of the fact that the compressed raw data stream 11 is usually smaller than the non-compressed raw data stream 9, a lower data rate is required to transfer the same information in a specific period of time. The data decompression device 12 decompresses the compressed raw data stream 11 to a decompressed compressed raw data stream 13, i.e., the original information content is restored. The decompression algorithm used is matched to the compression algorithm used, and it is possible to implement one algorithm in a hardwired electronic circuit while the other algorithm is implemented by execution of a computer program, in a computer. Finally, the decompressed raw data stream 13 is transferred to the image calculation tool 14 which, in turn, produces a medical image data set. The data compression device 10 and the data decompression device 12 can also be combined in one device 40 in order to obtain a medical image data set.

FIG. 3 shows an exemplary flowchart of an inventive method 1 for obtaining a medical image data set. The method 1 provides an image acquisition device, a data compression device, a data decompression device and an image calculation tool. In this embodiment, the method 1 comprises the processing steps S1 to S7. It begins "start" with processing step S1, and ends "end" following processing step S7. The individual processing steps involve:

S1) producing a raw data stream by means of the image acquisition device, wherein the raw data stream includes at least digital data of a medical raw image data set;

S2) receiving the raw data stream of the image acquisition device by means of the data compression device;

S3) compressing the raw data stream in the data compression device;

S4) transferring the compressed raw data stream to the data decompression device;

S5) decompressing the compressed raw data stream in the data decompression device;

S6) transferring the decompressed raw data stream to the image calculation tool and producing a medical image data set by operation of the image calculation tool on the decompressed raw data stream;

S7) monitoring a termination criterion. When the termination criterion is fulfilled, "Y", the method is concluded, "end", otherwise, "N", a branch to processing step S1 is made.

The termination criterion can involve monitoring for the end of the raw data stream. When the image acquisition device no longer supplies raw data, the end of the raw data stream has been reached, and thus the termination criterion is fulfilled and processing step 1 is concluded.

FIG. 4 is a schematic illustration of an embodiment of an inventive system 50 for obtaining a medical image data set which is connected to a Cloud Computing Network 30. The system 50 has an image acquisition device 8, for example, magnetic resonance imaging equipment, a data compression device 10, for example, an electronic circuit arranged, for example, in a housing of the image acquisition device 8, a data decompression device 12, an image calculation tool 14 and a calculation and representation tool 16, which can involve a commercial personal computer. The data compression device 12 and the image calculation tool 14 have been transferred to the so-called Cloud 30. The image acquisition device 8 generates a raw data stream 9 of a medical raw data set with a high data rate. The data compression device 10 compresses the raw data stream 9 to a compressed raw data stream 11, which has a data rate that is lower than the original raw data stream 9. Because of the lower data rate of the compressed raw data stream 11, the data with the smaller band width can be transferred to the Cloud 30. The processing steps "decompressing the compressed raw data stream 9" to a decompressed raw data stream 13 and "producing a medical image data set" are performed in the Cloud 30. Then the calculation and representation tool 16 receives the medical image data set 15 from the Cloud and represents it, for example, on a computer monitor. In this embodiment, instead of the original raw data stream 9, only the compressed raw data stream 11 has to be transferred to the Cloud.

FIG. 5 is a schematic illustration of an embodiment of a data decompression device 12, which has a storage device 18. The storage device 18, which can be implemented, for example, in the form of a hard drive memory or semiconductor memory, receives a compressed raw data stream 11 and stores it. This requires a considerably smaller storage capacity than for storing a non-compressed raw data stream. A decompression unit 20, which can be designed in the form of an electronic circuit or a computer program that is processed by a computer, receives the compressed raw data stream from the storage device 18, decompresses it and transfers a decompressed raw data stream 13, which corresponds in a loss-free compression to an original raw data stream 13, to subsequent computing devices. Subsequent computing devices, such as a reconstruction computer, do not have to process the data, i.e., the decompressed raw data stream, in real time. Therefore, these devices can be provided with less computing capacity than computing devices which have to process the original raw data stream.

In summary, further embodiments and advantages of the invention are described. The invention uses a data compression device and compression module, for example, for magnetic resonance tomographic image and subsequent image reconstruction. This results in a lower data volume and lower data rate for temporary storage or transfer of image data. As a result, it is possible to implement hardware components more cost-effective, for example, by means of fewer or slower hard drives in an RAID system, or the reconstruction on a separate computer, for example, a dedicated computer or a Cloud network, can start earlier and can be concluded faster, because with the same network connection the data is available faster.

In the following five examples, the acquisition of magnetic resonance tomographic images is described in the context of the present invention.

Example 1, "raw data RAID": raw data received in a reconstruction computer are often stored temporarily on a hard drive RAID, because more complex reconstruction methods are not able to process these data in real time. By means of an upstream compression, the requirement to this hardware can be considerably reduced, with regard to the number of hard drives, because of reducing the data volume, and/or with regard to the speed, because of the lower data rate. This makes it possible to reduce the costs, while being expandable for more possibilities, because a hardware solution cannot be arbitrarily extended so that, for example, the number and speed of the hard drives in a housing are limited.

Example 2, "private or public Cloud": when an MR image reconstruction is to take place in the Cloud, the data has to be transferred to the Cloud. Usually, the data rates to the Cloud cannot be arbitrarily increased because large distances have to be covered and the appropriate network connections are quite expensive, provided they are even available in the required speed. Therefore, an upstream MR raw data compression makes it possible to use a more reasonable network connection with the same effective performance, or the same network connection makes it possible to start the reconstruction earlier or to conclude it faster.

Example 3, "separate measurement and reconstruction computer": for special MR systems, the measurement computer, which receives the MR raw data in real time, and the reconstruction computer are separate units, which are connected via a very fast local network. For example, the local network can involve a 10G, an InfiniBand or any other known network, which is implemented in accordance with the maximum amount of data rates. Also in this case, the MR raw data compression interposed on the measurement computer results in a performance and/or cost advantage.

Example 4, "low cost system": this system does not involve a dedicated reconstruction computer. Therefore, the MR image reconstruction has to be performed, for example, on a calculation and representation tool or an operating computer, known as "host". Because of the fact that this involves a "low cost system", here only a standard Gigabit network connection would be used, which offers only limited performance with regard to the data rates. Because of the upstream MR raw data compression, this limit would be released.

Example 5, "computer bus": if the raw data compression does not take place via a computer program, which is performed by means of a CPU in a measurement computer, but is performed already by means of a dedicated electronic circuit, which processes and, for example, digitizes the raw data received, less data volume with a lower data rate has to be transferred from this hardware to a computer, which can be designed as a personal computer and further processes the data. As a result, the internal buses on the computer are noticeably relieved, i.e., it is possible to use more cost-effective devices or it is possible with the same data rate or bus use to implement more receiving channels.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for obtaining a medical image data set, using a medical raw data acquisition device, a data compression device, a data decompression device and an image calculation tool, said method comprising:

S1) producing a raw data stream by operation of the medical raw data acquisition device until an acquisition completion criterion occurs, wherein the raw data stream comprises at least digital data of a medical raw data set;

S2) during (S1), receiving the raw data stream of the image acquisition device with the data compression device;

S3) also during (S1) compressing the raw data stream in the data compression device;

S4) during at least a part of (S1), transferring the compressed raw data stream directly to the data decompression device without storage of the compressed raw data stream;

S5) decompressing the compressed raw data stream in the data decompression device;

S6) transferring the decompressed raw data stream directly to the image calculation tool without storage of the decompressed data stream, and producing a medical image data set by execution of a reconstruction algorithm of the image calculation tool on the decompressed raw data stream, and making the medical image data set available from the image calculation tool in electronic form as a data file.

2. A method according to claim 1, comprising performing S1 to S6 repeatedly until a termination criterion tested in S6 has been fulfilled.

3. A method according to claim 1 comprising compressing the raw data in the data compression device, using a loss-free compression method.

4. A method according to claim 1, wherein the raw data stream comprises digital data of a medical image data set and additional data, said additional data including information of the image acquisition device and/or additional data regarding the production of the raw data stream.

5. A method according to claim 4, comprising compressing the digital data of a medical image data set using a lossy compression method in said compression device, and comprising the additional data using a loss-free compression method in the compression device.

6. A method according to claim 1, wherein the data decompression device and the image calculation tool are part of a Cloud Computing Network and, after S6, transferring the medical image data set to a calculation and representation tool.

7. A method according to claim 1, comprising compressing the raw data stream by executing a software program in the data compression device and/or decompressing the compressed raw data stream by executing a software program in the data decompression device.

8. A device for obtaining a medical image data set, comprising:

a data compression device configured to receive a raw data stream produced by operation of a medical raw data acquisition device until an acquisition completion criterion occurs, said raw data stream comprising at least digital data of a medical raw data set, said compression device being configured to receive said raw data stream during production thereof by the raw data acquisition device until occurrence of said acquisition completion criterion, and said data compression device being configured to compress the raw data stream during production thereof by said medical raw data acquisition device until said occurrence of said acquisition completion criterion, thereby generating a compressed raw data stream;

a data decompression device in direct communication with said data compression device;

said data compression device being configured to transfer, during at least a part of the production of said raw data stream by said medical raw data acquisition device, the compressed raw data stream directly to the data decompression device without storage of the compressed raw data stream;

said data decompression device being configured to decompress the transferred, compressed raw data stream, thereby producing a decompressed raw data stream;

a reconstruction computer in direct communication with said data decompression device;

said data decompression device being configured to transfer the decompressed raw data stream directly to the image reconstruction computer without storage of the decompressed raw data stream; and said reconstruction computer being configured to execute a reconstruction algorithm that operates on said decompressed raw data stream to produce a medical image data set, and to make said medical image data set available from the reconstruction computer in electronic form as a data file.

9. A system for obtaining a medical image data set, comprising:

a medical raw data acquisition device configured to produce a raw data stream of medical raw data acquired from an examination subject that interacts with the medical raw data acquisition device, until an acquisition completion criterion occurs, said raw data stream comprising at least digital data of a medical raw data set;

a data compression device configured to receive a raw data stream produced by operation of a medical raw data acquisition device until an acquisition completion criterion occurs, said raw data stream comprising at least digital data of a medical raw data set, said data compression device being configured to receive said raw data stream during production thereof by the raw data acquisition device until occurrence of said acquisition completion criterion, and said compression device being configured to compress the raw data stream during production thereof by said medical raw data acquisition device until said occurrence of said acquisition completion criterion, thereby generating a compressed raw data stream;

a data decompression device in direct communication with said data compression device;

said data compression device being configured to transfer, during at least a part of the production of said raw data stream by said medical raw data acquisition device, the compressed raw data stream directly to the data decompression device without storage of the compressed raw data stream;

said data decompression device being configured to decompress the transferred, compressed raw data stream, thereby producing a decompressed raw data stream;

a reconstruction computer in direct communication with said data decompression device;

said data decompression device being configured to transfer the decompressed raw data stream directly to the image reconstruction computer without storage of the decompressed raw data stream; and said reconstruction computer being configured to execute a reconstruction algorithm that operates on said decompressed raw data stream to produce a medical image data set, and to make said medical image data set available from the reconstruction computer in electronic form as a data file.

10. A system as claimed in claim 9 wherein said medical raw data acquisition device is a magnetic resonance data acquisition scanner.

* * * * *